United States Patent
Morman

(10) Patent No.: US 6,843,872 B2
(45) Date of Patent: Jan. 18, 2005

(54) NECK BONDED AND STRETCH BONDED LAMINATES WITH PERFORATED NONWOVENS AND METHOD OF MAKING

(75) Inventor: Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 234 days.

(21) Appl. No.: 10/034,353

(22) Filed: Dec. 28, 2001

(65) Prior Publication Data

US 2003/0124306 A1 Jul. 3, 2003

(51) Int. Cl.$^7$ ................................................ B32B 31/00
(52) U.S. Cl. ........................ 156/163; 156/164; 156/199; 156/252; 156/257; 156/268; 156/269; 156/270; 428/138; 442/381; 442/394; 604/385.01
(58) Field of Search ................................. 156/269, 270, 156/163, 164, 199, 252, 257, 268; 604/366, 370, 385.01; 442/381, 394; 428/138

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,652,487 A | 3/1987 | Morman |
| 4,655,760 A | 4/1987 | Morman et al. |
| 4,657,802 A | 4/1987 | Morman |
| 4,692,368 A | 9/1987 | Taylor et al. |
| 4,720,415 A | 1/1988 | Vander Wielen et al. |
| 4,781,966 A | 11/1988 | Taylor |
| 4,789,699 A | 12/1988 | Kieffer et al. |
| 4,965,122 A | 10/1990 | Morman |
| 4,981,747 A | 1/1991 | Morman |
| 5,108,820 A | 4/1992 | Kaneko et al. |
| 5,114,781 A | 5/1992 | Morman |
| 5,116,662 A | 5/1992 | Morman |
| 5,226,992 A | 7/1993 | Morman |
| 5,336,545 A | 8/1994 | Morman |
| 5,336,552 A | 8/1994 | Strack et al. |
| 5,382,400 A | 1/1995 | Pike et al. |
| 5,804,021 A | 9/1998 | Abuto et al. |
| 2002/0022424 A1 * | 2/2002 | Meece et al. ................ 442/328 |

FOREIGN PATENT DOCUMENTS

| | | |
|---|---|---|
| EP | 0 122 085 A1 | 10/1984 |
| EP | 0 138 225 A2 | 10/1984 |
| EP | 0 191 355 A1 | 8/1986 |
| EP | 0 217 032 A2 | 4/1987 |
| EP | 0 331 018 A1 | 9/1989 |
| EP | 0 626 160 B1 | 1/1998 |
| GB | 2 302 811 A | 6/1996 |
| JP | 11-291372 | 10/1999 |
| JP | 2001-30394 | 2/2001 |
| WO | WO 95/16425 | 6/1995 |
| WO | WO 95/32327 | 11/1995 |
| WO | WO 03/003961 | 1/2003 |
| WO | WO 03/057481 | 7/2003 |

\* cited by examiner

Primary Examiner—Linda Gray
(74) Attorney, Agent, or Firm—Pauley Petersen & Erickson

(57) ABSTRACT

An elastic laminate of a necked, or otherwise inherently stretchable, and perforated nonwoven web layer and an unperforated elastic film layer and methods of making the laminate are disclosed. An elastic laminate according to the present invention may utilize both the stretch gained from the necking, as well as providing increased ability of the necked nonwoven to stretch due to the perforations, cumulatively resulting in high stretch of the elastic laminate in one or more directions.

20 Claims, 5 Drawing Sheets

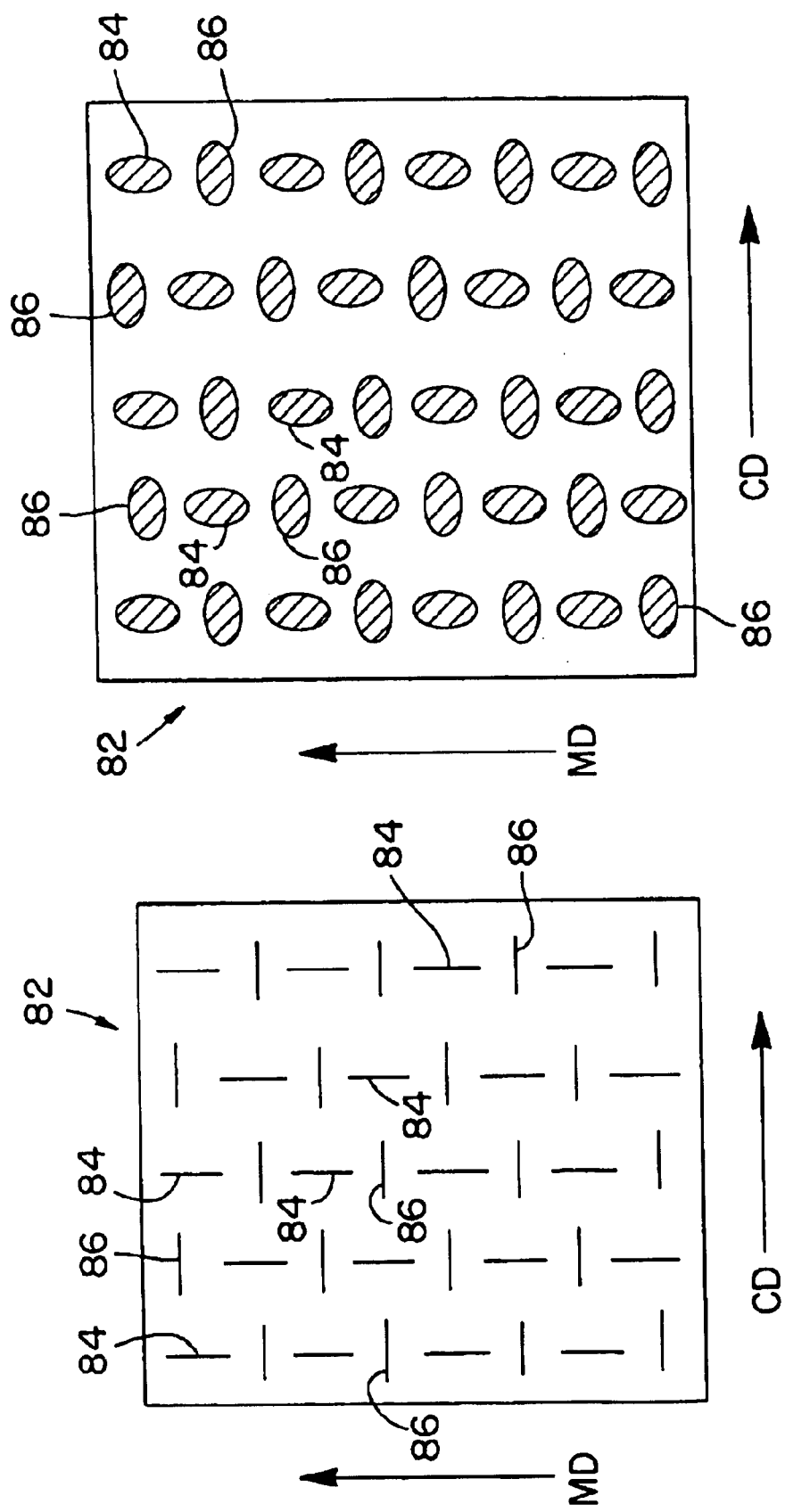

NECK BONDED AND STRETCH BONDED LAMINATES WITH PERFORATED NONWOVENS AND METHOD OF MAKING

BACKGROUND

In the field of nonwoven web/elastic material laminates (hereinafter referred to as "elastic laminates" for simplicity) garment panels for disposable or limited use garments, some desirable qualities may include light weight, good skin feel, exterior abrasion resistance, and good flexibility dependent upon the application. Generally such elastic laminates may be made with a first nonwoven facing of desired characteristics laminated to an elastic film.

However, in the past, the ability of the nonwoven to stretch has limited the suitability of such elastic laminates for various applications because a laminate will only stretch to the extent of its least extendible layer. Various techniques have been utilized in the art in order to overcome such limitations.

For example, perforations have been applied to the nonwovens in either the machine direction or the cross direction of the nonwoven in order to try and increase the range of extendibility of the nonwovens in the elastic film laminates. U.S. Pat. No. 5,804,021 issued Sep. 8, 1998 to Abuto et al. illustrates one such teaching. It is also known to perforate the entire elastic film laminate. However, this technique leads to a great reduction in the retractive force of the elastic film.

As an alternative to perforating, necked nonwoven webs are also known wherein the nonwoven is extended in the machine direction to decrease its cross direction dimension in a process known as necking. The necked nonwoven is then laminated to an elastic material which holds the necked nonwoven at the reduced cross direction dimension until force is applied whereby the nonwoven may extend out to its pre-necked dimension. U.S. Pat. No. 4,981,747 issued Jan. 1, 1991 to Morman illustrates one such teaching, and is incorporated herein by reference in its entirety.

Both the perforating methods and the necking methods may have limitations for the making of elastic laminates in terms of degree or direction of stretchability of the laminate, or the economy of manufacture of the elastic laminates, or both, thereby limiting the applications to which such laminates may be put.

Thus, there is need to provide further alternative methods for the production of economical elastic laminates having superior stretching abilities.

SUMMARY

The present invention solves the above-stated needs in the art by elastic laminates made, in one aspect of the invention, from necked and perforated nonwoven facings and not-perforated, or un-perforated, elastic films, i.e. films substantially devoid of perforations. Thus an elastic laminate according to the present invention may utilize both the extensibility gained from the necking of its component parts, as well as providing increased ability of the necked nonwoven to extend due to the perforations, cumulatively resulting in a high extensibility of the elastic laminate in one or more directions. For example, a hypothetical nonwoven web which has been necked from four inches to two inches in its transverse dimension would normally have an extensibility back the original four inch width, or extensibility of one hundred percent. However, when the nonwoven is first perforated at its four inch width so that, e.g., it may achieve an extensibility up to six inches, and then necked, e.g. down to two inches, the necked and perforated two inch web may expand to six inches, thereby resulting in a two hundred percent extensibility of the necked and perforated two inch web. It will be appreciated that the total percentage of extensibility may be varied by adjusting the values of the above example, which are used only for illustration of the principles of the present invention. Thus, a laminate according to the present invention may be used in applications such as, e.g., disposable training pant side panels or diaper fastening panels where the degree of stretch required previously prohibited use of such elastic laminates.

In various aspects of the invention the nonwoven laminates may be perforated before or after necking. In other aspects of the invention the nonwovens may be a necked spunbond or other nonwoven. In some aspects of the invention the nonwoven will have various degrees and orientations of extensibility before being applied to the elastic film. In other aspects of the invention various patterns and orientations of perforations are made in the nonwoven layer. Further, the elastic film may be utilized as the strength-providing member of the laminate resulting in a wide range of nonwoven choices for the designer, such as lighter nonwoven facings. Also, by freeing certain areas of elastic from contact with the perforated area of the nonwoven web, overall elasticity may be improved over that of known laminates.

DEFINITIONS

Conventionally, "stretch bonded" refers to an elastic member being bonded to another member while the elastic member is extended at least about 25 percent of its relaxed length. "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al. Other composite elastic materials are disclosed in U.S. Pat. No. 4,789,699 to Kieffer et al. and U.S. Pat. No. 4,781,966 to Taylor. Further reference will be had to U.S. Pat. Nos. 4,652,487 and 4,657,802 to Morman and 4,655,760 to Morman et al., which are incorporated herein by reference in their entirety.

Conventionally, "neck bonded" refers to an elastic member being bonded to a non-elastic member while the non-elastic member is extended and necked. "Neck bonded laminate" refers to a composite material having at least two layers in which one layer is a necked, non-elastic layer and the other layer is an elastic layer. The layers are joined together when the non-elastic layer is in an extended and necked condition. Examples of neck-bonded laminates are such as those described in U.S. Pat. Nos. 5,226,992; 4,981,747; 4,965,122 and 5,336,545 to Morman, all of which are incorporated herein by reference in their entirety.

Conventionally, "necked stretch bonded" refers to an elastic member being bonded to a non-elastic member while the non-elastic member is extended and necked and the elastic member is at least extended. "Necked stretch bonded laminate" refers to a composite material having at least two layers in which one layer is a necked, non-elastic layer and the other layer is a stretched, and sometimes necked, elastic layer. The layers are joined together when in their extended (and necked) conditions. Examples of necked stretch bonded laminates are described in U.S. Pat. Nos. 5,114,781 and 5,116,662 to Morman, which are incorporated herein by reference in their entirety.

The term "bicomponent filaments" or "bicomponent fibers" refers to fibers which have been formed from at least two polymers extruded from at least two separate extruders but spun together to form one fiber and may also be referred to herein as "conjugate" or "multicomponent" fibers. "Bicomponent" is not meant to be limiting to only two constituent polymers unless other specifically indicated. The polymers are arranged in substantially constantly positioned distinct zones across the cross-section of the bicomponent fibers and extend continuously along the length of the bicomponent fibers. The configuration of such a bicomponent fiber may be, for example, a sheath-core arrangement wherein one polymer is surrounded by another, or may be a side-by-side, A/B, arrangement or an A/B/A, side-by-side(-by-side), arrangement. Bicomponent fibers are generally taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

As used herein, the terms "elastic", "elastomeric", and forms thereof, mean any material which, upon application of a biasing force, is stretchable, that is, elongatable or extensible, and which will substantially return to its original shape upon release of the stretching, elongating force. The term may include precursor elastomerics which are heat activated or otherwise subsequently treated after application to a precursor diaper structure to induce elasticity. The term "extendable" refers to a material which is stretchable in at least one direction but which does not necessarily have sufficient recovery to be considered elastic.

The term "perforate" or "perforated" refers to cuts or holes in a web which are contained within the boundaries of the web and do not extend between and through the cross direction or the machine direction margins of the web.

The term "nonwoven fabric" or "nonwoven web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air-laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein the term "elastic material" or "elastic film" will include such materials as films, fibers, scrims, foams, or other layers of elastic material, As used herein, the term "machine direction" or MD means the length of a fabric in the direction in which it is produced. The term "cross direction" or "cross machine direction" or CD means the width of fabric, i.e. a direction generally perpendicular to the machine direction.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

As used herein, the term "neck" or "neck stretch" interchangeably means that the fabric is extended under conditions reducing its width or its transverse dimension. The controlled extension may take place under cool temperatures, room temperature or greater temperatures and is limited to an increase in overall dimension in the direction being extended up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, extends the fabric and generates the tension needed to elongate and neck the fabric. U.S. Pat. No. 4,965,122, issued Oct. 23, 1990 to Morman, which discloses a process for providing a reversibly necked nonwoven material which may include necking the material, then heating the necked material, followed by cooling.

As used herein, the term "neckable material or layer" means any material which can be necked such as a nonwoven, woven, or knitted material. As used herein, the term "necked material" refers to any material which has been extended in at least one dimension, (e.g. lengthwise), reducing the transverse dimension, (e.g. width), such that when the extending force is removed, the material can be pulled back, or relax, to its original width. The necked material typically has a higher basis weight per unit area than the un-necked material. When the necked material returns to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the neckable backsheet 30 of the various aspects of the present invention may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percentage of necking (percent neck) can be determined in accordance with the description in the above-mentioned U.S. Pat. No. 4,965,122.

The term "polymer" generally includes without limitation homopolymers, copolymers (including, for example, block, graft, random and alternating copolymers), terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

"Personal care product" or "personal care absorbent article" means diapers, wipes, training pants, absorbent underpants, adult incontinence products, feminine hygiene products, wound care items like bandages, and other like articles.

The term "spunbond fibers" refers to small diameter fibers which are formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky when they are deposited onto a collecting surface. Spunbond fibers are generally continuous and usually have average diameters larger than meltblown fibers, and more particularly, generally between about 10 and 30 microns.

The term "substantially continuous filaments" or "substantially continuous fibers" refers to filaments or fibers prepared by extrusion from a spinneret, including without limitation spunbond and meltblown fibers, which are not cut from their original length prior to being formed into a nonwoven web or fabric. Substantially continuous filaments or fibers may have average lengths ranging from greater than about 15 cm to more than one meter, and up to, or greater than, the length of the nonwoven web or fabric being formed. The definition of "substantially continuous filaments" (or fibers) includes those filaments or fibers which are not cut prior to being formed into a nonwoven web or fabric, but which are later cut when the nonwoven web or fabric is cut.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

BRIEF DESCRIPTION OF THE DRAWINGS

The accompanying drawings are presented as an aid to explanation and understanding of various aspects of the present invention only and are not to be taken as limiting the present invention. The drawings are not necessarily to scale, nor should they be taken as photographically accurate depictions of real objects unless otherwise stated.

FIG. 4 illustrates a possible perforation pattern in the nonwoven using both machine direction and cross direction oriented perforations.

FIG. 5 illustrates the effect on the perforations of the fabric of FIG. 4 after tension is applied.

DETAILED DESCRIPTION

Certain aspects and embodiments of the invention will be described in the context of disposable absorbent articles, and may more particularly be referred to, without limitation and by way of illustration, as a disposable training pant garment or swim wear garment with elastic side panels. It is, however, readily apparent that aspects of the present invention can also be employed to produce other elasticized areas and for other garment or personal care article types, such as feminine care articles, various incontinence garments, medical garments and any other disposable garments, whether absorbent or not, needing an easily manufactured elasticized area. Typically, such disposable garments are intended for limited use and are not intended to be laundered or otherwise cleaned for reuse. A disposable training pant, for example, is discarded after it has become soiled by the wearer.

Figure 1:
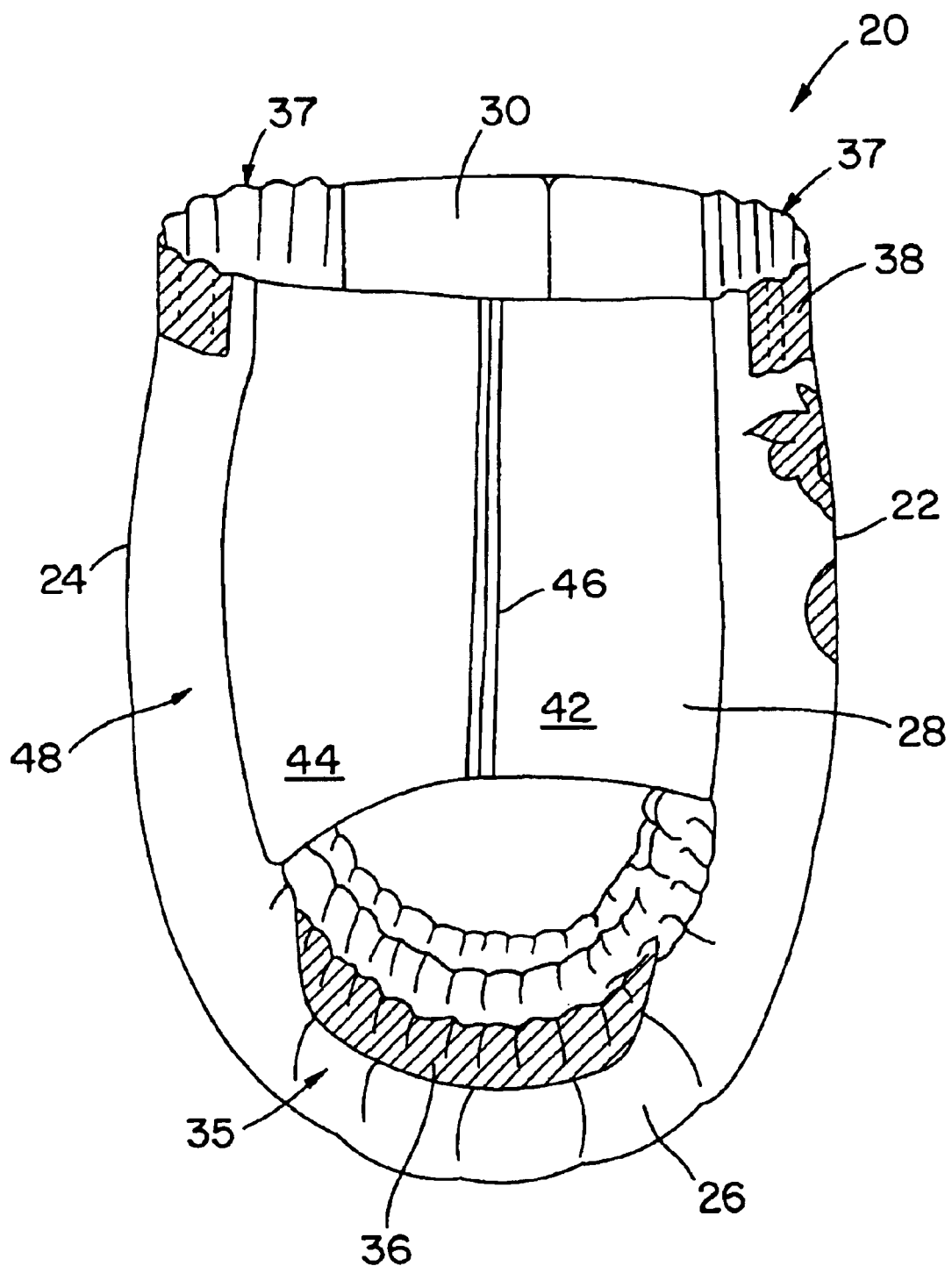
FIG. 1 illustrates a training pant/swim pant which may utilize the elastic laminate of the present invention.

With reference to FIG. 1, the garment 20 generally defines a front waist section 22, a rear waist section 24, and a crotch 26 which interconnects the front and rear waist sections. The front and rear waist sections 22 and 24 include the general portions of the garment which are constructed to extend over the wearer's front and rear abdominal regions, respectively, during use. Elasticized side panels 28, 30, as further explained below, connect the front and rear waist sections 22, 24, respectively. The crotch 26 of the garment includes the general portion of the garment that is constructed to extend through the wearer's crotch region between the legs.

To provide improved fit and to help reduce leakage of body exudates from the garment 20, the garment leg cuffs 35 and waist margins 37 may be elasticized with suitable elastic members. For example, as illustrated in FIG. 1, the garment 20 may include leg elastics 36 which are constructed to operably tension the side margins of the garment 20 to provide elasticized leg bands which can closely fit around the legs of the wearer to reduce leakage and provide improved comfort and appearance. Waist elastics 38 may be employed to elasticize the waist margins 37 of the garment 20 to provide elasticity to the waistband. The waist elastics 38 are configured to help provide a resilient, comfortably close fit around the waist of the wearer.

Referencing FIG. 1, the side panels 28, 30 are also elasticized to provide improved fit and conformance to the wearer. Each side panel, e.g., side panel 28, is composed of a first portion 42, and a second portion 44. The first portion 42 is bonded to the front waist section 22 by any known means such as ultrasonic bonding, adhesives, etc. Likewise the second portion 44 is bonded to the back waist section 24 in similar matter. The free ends of the side panel portions not bonded to the waist sections are then bonded in a standing butt seam 46 to create a side panel area 48. As used herein, the term "standing butt seam" refers to a seam wherein two separate pieces of substrate are bonded together face-to-face or back-to-back in close proximity to an outer edge of each of the pieces of substrate, and the outer edges of the pieces of substrate project outward from the finished product, placing the seam in peel, as opposed to shearing strain. The seam 46 may be substantially permanent or easily separable depending on the garment application.

Figure 2:
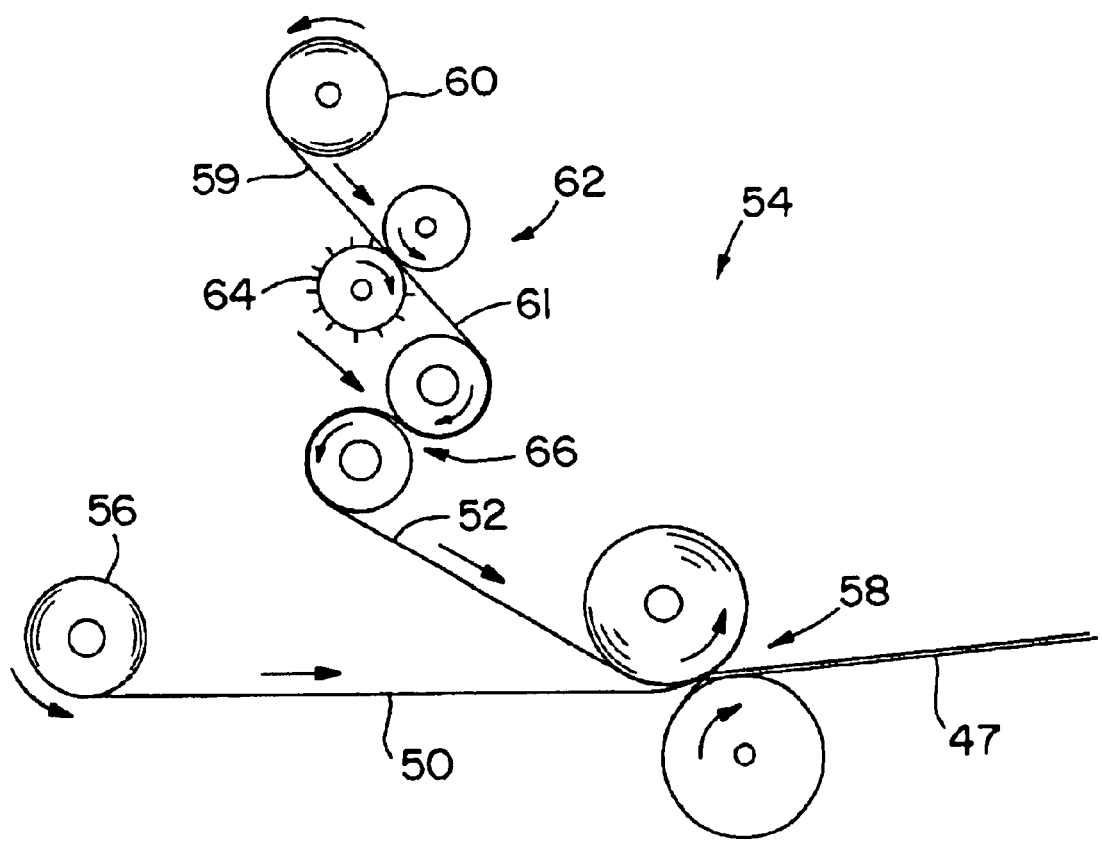
FIG. 2 illustrates a process for making an elastic laminate of the present invention wherein the elastic film layer is not stretched prior to lamination to the nonwoven.

Referencing FIG. 2, an exemplary material, or laminate, 47 for the side panel portions is made from elastic film and perforated and necked nonwoven web 52 by laminating apparatus 54 in a neck bonded style. The elastic film 50, such as a film of KRATON G-1657 elastic block co-polymer from KRATON Polymers of Houston, Tex., is taken from a first supply roll 56 rotating at about the same speed as the calendar rolls 58 so as to not tension the elastic film 50 before lamination to the perforated and necked nonwoven 52. The nonwoven web 59, e.g., a 0.4 osy polypropylene or bicomponent spunbond or meltblown nonwoven web of substantially continuous fibers, is drawn from a supply roll 60 by a first pair of rollers 62, one of which 64 is configured to perforate the nonwoven web 59 in the pattern indicated by FIG. 4. The perforated web 61 is then further tensioned and necked by a second pair of rollers 66 moving at higher speed than the first pair of tensioning rollers 62. The necking tension on the perforated and necked nonwoven 52 is then maintained by calender rolls 58 as the nonwoven 52 and the nonstretched elastic film 50 are joined by nipping through the calender rolls 58. The calendar rolls may be used to heat fuse the laminate layers by pattern bonding, a heat activated adhesive (not shown) may be applied between the layers, or other such methods as known in the art may be utilized.

Figure 3:
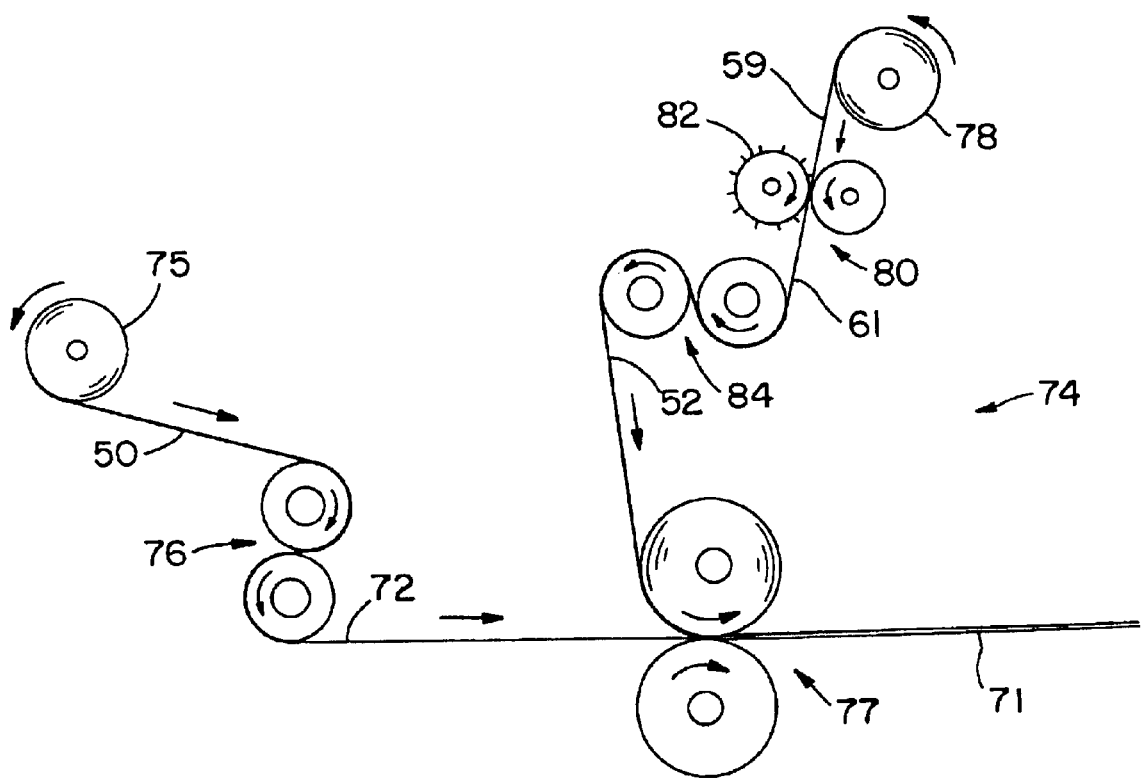
FIG. 3 illustrates a process for making an elastic laminate of the present invention wherein the elastic film layer is stretched prior to lamination to the nonwoven.

Referencing FIG. 3, a second exemplary material, or laminate, 71 for the side panel portions is made from a tensioned elastic film 72 and perforated and necked nonwoven 52 by a laminating apparatus 74 in a stretch bonded style. The elastic film 50, such as a film of KRATON G-1657 elastic block co-polymer is taken from a first supply roll 75 rotating at a slower speed than the first take-up or tensioning rolls 76. The tensioning rolls 76 are moving at a slower speed than the calender rolls 77 so as to tension the elastic film 50 before lamination to the perforated and necked nonwoven 52. The nonwoven web 59, e.g., a 0.4 osy polypropylene spunbond nonwoven web, is drawn from a supply roll 78 by a first pair of rollers 80, one of which 82 is configured to perforate the nonwoven web 59 in the pattern indicated by FIG. 4. The perforated web 61 is then further tensioned and necked by a second pair of rollers 84 moving at higher speed than the first pair of tensioning rollers 62. The necking tension on the perforated and necked nonwoven 52 is then maintained by calender rolls 58 as the perforated and necked nonwoven 52 and the stretched elastic film 50 are joined by nipping through the calender rolls 77. The calendar rolls 77 may be used to heat fuse the laminate layers by pattern bonding, a heat activated adhesive (not shown) may be applied between the layers, or other such methods as known in the art may be utilized. It will of course be possible to produce laminates having more than two webs. It would be further possible to arrange the perforations of a plurality of nonwovens in such a manner as to accommodate various alternative stretching abilities for the elastic laminate.

Referencing FIG. 4, a perforated but unstretched nonwoven 82 such as for example may be had from the perforating roller 64, 82 of FIGS. 2 and 3, respectively, has a machine direction MD and a cross (machine) direction CD. Machine direction oriented perforations, collectively 84, are placed in the nonwoven web 82 so as to facilitate extending of the nonwoven in the cross direction. Cross direction oriented perforations, collectively 86, are placed in the nonwoven web 82 so as to facilitate extending of the nonwoven in the machine direction.

Referencing FIG. 5, as tension is applied in the cross direction, the machine direction perforations 84 will expand allowing greater expandability of the web 82 in the cross direction. As tension is applied in the machine direction, the cross direction perforations 86 will expand allowing greater expandability of the web 82 in the machine direction.

In an alternative aspect of the invention, a necked and set spunbond material, having stretch or extensibility in the cross direction, may be creped, i.e. a form of mechanical gathering, as per the teachings of U.S. Pat. No. 3,668,054 to Stumpf, to also provide machine direction stretch. The setting of the necked material may occur before or during the creping process. The creped and necked material can then be perforated per the apparatus of FIG. 2 or 3 to provide a material with high MD and CD extendibility. Alternatively, a creped material, not previously necked, and therefore having extendibility primarily in the MD, may be used per the teachings of the present invention. Per the above discussion, either of these creped materials may be perforated with MD slits to provide additional CD elongation, CD slits to provide additional MD elongation, or MD and CD slits to provide additional MD and CD extendibility. The perforated creped material may be laminated to an elastic film which is tensioned or untensioned to provide a laminate with elasticity in more than one axis. It will generally be appreciated that dependent upon the amount and direction of the stretchability of the starting web, and the subsequent patterns of perforations applied thereto, various combinations, degrees, and orientations of material stretchability and elasticity may be had according to the teachings of the present invention. Accordingly, the present invention is not to taken as limited to the illustrative embodiments or exemplary materials set forth herein.

Figure 6:
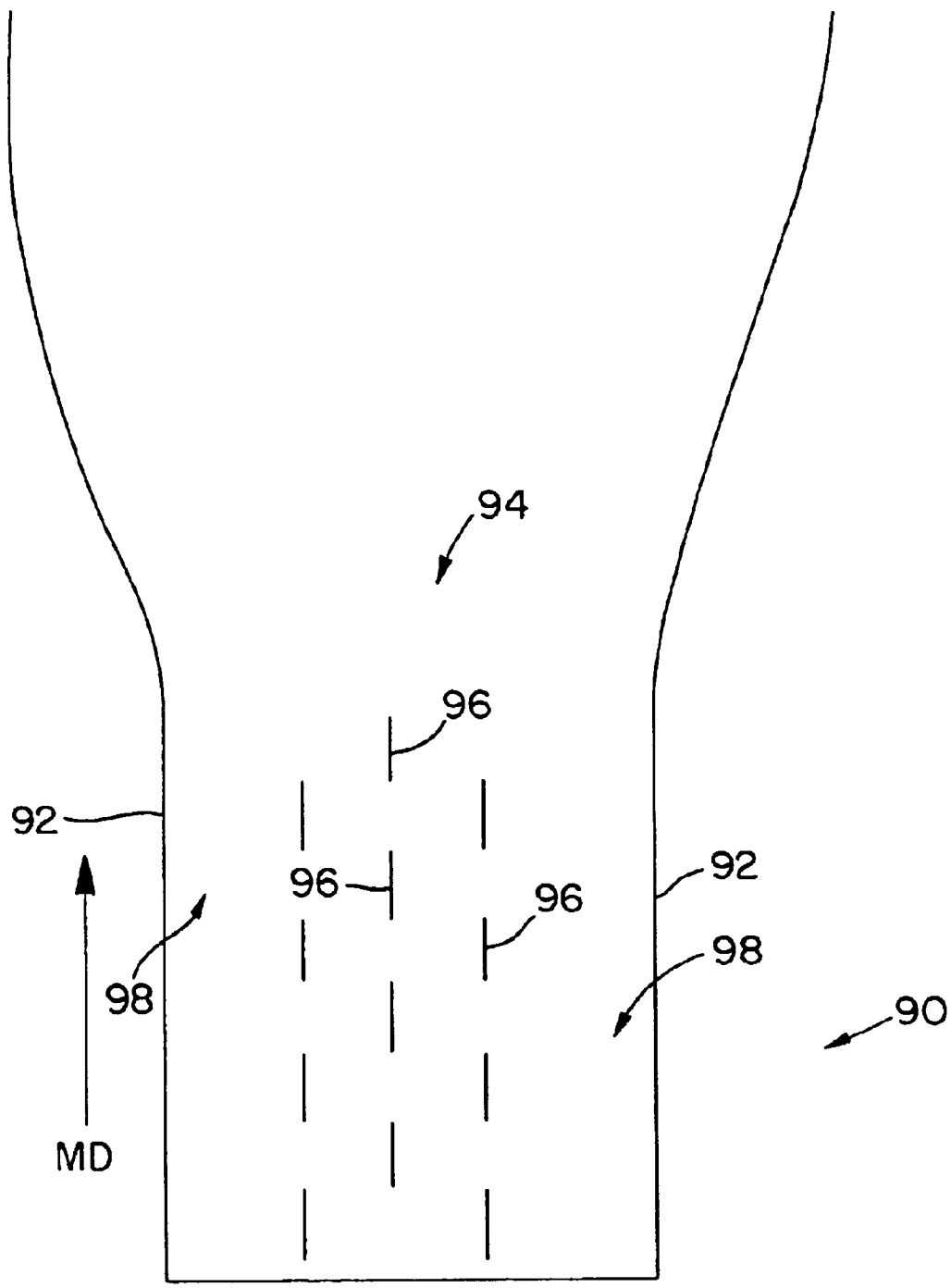
FIG. 6 illustrates a necked nonwoven having perforations placed in selected areas and being left unperforated in other areas.

In another alternative aspect of the invention, the perforations may be selectively placed within certain regions of the necked nonwoven to provide for a more uniform elasticity of the laminate while other regions remain non-perforated. Referencing FIG. 6, a necked material 90, prior to any perforation, will generally have an inherently higher extensibility at its transverse margins 92 than in its center region 94. To provide greater extension for the center region 94, machine direction perforations, collectively 96, are selectively placed in the center region 94, while the transverse margin areas 98 are not perforated, thus evening out any non-uniformities in the extensibility of the nonwoven, necked material. Alternatively, variants of this technique may be used to produce deliberately non-uniform areas of extensibility in the nonwoven web.

Having thus described a highly expandable elastic laminate containing at least one necked and perforated web and an elastic film, it will be appreciated that many variations thereon may occur to the person having ordinary skill in the art. Thus, the invention is intended to be limited only by the appended claims and not by the exemplary embodiments and aspects put forth herein.

What is claimed is:

1. A high-stretch elastic laminate, comprising:
    a) one or more necked nonwoven webs having a plurality of perforations; and
    an elastic film substantially devoid of perforations bonded to the one or more necked, perforated nonwoven webs.

2. The high-stretch elastic laminate of claim 1, wherein the nonwoven web is a spunbond nonwoven web.

3. The high-stretch elastic laminate of claim 1, wherein the perforations of the nonwoven web extend in the cross direction.

4. The high-stretch elastic laminate of claim 1, wherein the perforations of the nonwoven web extend in the machine direction.

5. The high-stretch elastic laminate of claim 1, wherein the nonwoven web is perforated before being necked.

6. The high-stretch elastic laminate of claim 1, wherein the nonwoven web is perforated after being necked.

7. The high-stretch elastic laminate of claim 1, wherein the nonwoven web is selectively perforated in some regions and left un-perforated in other regions.

8. The high-stretch elastic laminate of claim 1 wherein the elastic film is an elastomeric block copolymer film.

9. The high-stretch elastic laminate of claim 1 wherein the laminate is one of a stretch bonded laminate, a neck bonded laminate, a necked stretch bonded laminate, or a creped nonwoven/elastic film laminate.

10. A method of making a high-stretch elastic laminate of a necked nonwoven web and an elastic film substantially devoid of perforations, comprising:

a) necking a nonwoven web b) placing a plurality of perforations in the nonwoven web; and c) bonding an elastic film substantially devoid of perforations to the necked and perforated nonwoven web.

11. The method of making a high-stretch elastic laminate of claim 10, wherein the nonwoven web is a spunbond nonwoven web.

12. The method of making a high-stretch elastic laminate of claim 10, wherein the perforations of the nonwoven web extend in the cross direction.

13. The method of making a high-stretch elastic laminate of claim 10, wherein the perforations of the nonwoven web extend in the machine direction.

14. The method of making a high-stretch elastic laminate of claim 10, wherein the nonwoven web is perforated before being necked.

15. The method of making a high-stretch elastic laminate of claim 10, wherein the nonwoven web is perforated after being necked.

16. The method of making a high-stretch elastic laminate of claim 10, wherein the nonwoven web is selectively perforated in some regions and left un-perforated in other regions.

17. The method of making a high-stretch elastic laminate of claim 10 wherein the elastic film is an elastomeric block copolymer film.

18. The method of making a high-stretch elastic laminate of claim 10 wherein the laminate is made as one of a stretch bonded laminate, a neck bonded laminate, a necked stretch bonded laminate, or a creped nonwoven, elastic film laminate.

19. A side panel for a personal care garment made from the high-stretch elastic laminate of claim 1.

20. A side panel for a personal care garment made according to the method of claim 10.

* * * * *